(12) United States Patent
Rattner

(10) Patent No.: US 6,213,638 B1
(45) Date of Patent: Apr. 10, 2001

(54) MEDICAL DEVICE WITH AUTOMATICALLY CONTROLLED RECTILINEAR DISPLACEMENT OF A DEVICE COMPONENT RELATIVE TO A LINE

(75) Inventor: Manfred Rattner, Grossenseebach (DE)

(73) Assignee: Siemens Aktiengesellscaft, Munich (DE)

( * ) Notice: Subject to any disclaimer, the term of this patent is extended or adjusted under 35 U.S.C. 154(b) by 0 days.

(21) Appl. No.: 09/335,148

(22) Filed: Jun. 17, 1999

(30) Foreign Application Priority Data

Jun. 17, 1998 (DE) ................................. 198 27 022

(51) Int. Cl.[7] ........................................... A61B 6/08
(52) U.S. Cl. ............................ 378/198; 378/205; 378/206
(58) Field of Search ................................ 378/198, 205, 378/206

(56) References Cited

U.S. PATENT DOCUMENTS 5,048,070 * 9/1991 Maehama et al. ............... 378/197
5,745,548   4/1998 Dobbs et al. ..................... 378/207
6,050,724 * 4/2000 Schmitz et al. .................. 378/205
6,120,180 * 9/2000 Graumann ........................ 378/206

FOREIGN PATENT DOCUMENTS 196 11 705   10/1997 (DE) .

* cited by examiner

Primary Examiner—David V. Bruce
Assistant Examiner—Allen C. Ho
(74) Attorney, Agent, or Firm—Schiff Hardin & Waite

(57) ABSTRACT

A medical device has a device component that is connected to a mount, which includes elements that can be moved relative to one another in a motorized fashion, and a control and computing unit which controls the motorized relative movements of the elements. A position identification arrangement is allocated to the control and computing unit which supplies signals to permit determination by the control and computing unit of lines in space with different directions, along which the device component can be moved in a motorized fashion, at least indirectly, by the mount.

9 Claims, 3 Drawing Sheets

MEDICAL DEVICE WITH AUTOMATICALLY CONTROLLED RECTILINEAR DISPLACEMENT OF A DEVICE COMPONENT RELATIVE TO A LINE

BACKGROUND OF THE INVENTION

1. Field of the Invention

The present invention relates to a medical device of the type having at least one device component, which is connected to a mount having two elements that can be displaced relative to each other in a motorized fashion, and a control and computing unit which controls the motorized relative movements.

2. Description of the Prior Art

German OS 196 11 705 teaches an X-ray pickup system with a first stand, which can be displaced in three dimensions in space and at which an X-ray receiver is arranged, and a second stand, at which an X-ray source is arranged. Sensors detect the position of the X-ray receiver in space. A computer forms a control signal, with the aid of the sensor signals fed to it, for the displacement of the X-ray source, so that the X-ray source is automatically oriented to the X-ray receiver. Due to the arrangement of the X-ray receiver separately from the X-ray source, the X-ray receiver can also be operated as an X-ray pickup unit with other X-ray sources.

U.S. Pat. No. 5,745,548 teaches a system and a method for pre-calibrating the position of the focal spot of an X-ray tube prior to its installation in a computed tomography device. In a test device which copies the exposure of the X-ray tube in the computed tomography device, at least three beam paths are defined using a system of openings, these paths intersecting in the desired position of the focal spot on the anode of the X-ray tube. In the beam paths, X-ray detectors are arranged by means of which the deviation of the focal spot from its desired position can be determined and the desired location of the focal spot can be set.

Many imaging systems have a movable C-arm X-ray device which has a C-arm which is supported at a mount and at which an X-ray system, comprising an X-ray source and an X-ray receiver, is arranged. The C-arm is usually supported at the mount so as to be displaceable along its perimeter for X-ray pickups at different directions of projection. The mount is usually formed by a number of elements which can be moved relative to one another in a motorized fashion for vertical and horizontal displacement of the C-arm. In this way, the C-arm X-ray device can be used for a number of different medical examinations.

The use of this type of C-arm X-ray device is problematic, however, or has significant difficulties, if the X-ray device (e.g. for diagnostic purposes in orthopedics) is to be used for a series of X-ray pickups of a body part of a patient, whereby, in the course of the X-ray pickups, the X-ray system of the X-ray device must be moved as linearly as possible directly or indirectly along a line in space. A linear movement of the X-ray system along a horizontally extending line in space in the course of a series of X-ray pickups is practically impossible with known C-arm X-ray devices.

SUMMARY OF THE INVENTION

An object of the present invention is to provide a medical device of the type described above wherein the device component can be moved at least indirectly along a line in space in a linear fashion.

This object is inventively achieved in a medical device having a device component which is connected to a mount and which carries an X-ray source and an X-ray receiver, the mount having elements which can be moved relative to one another in a motorized fashion, and a control and computing unit, which controls the relative movements of the elements, with line identifiers allocated to the control and computing unit which permit lines to be defined in space proceeding along different directions, along which the device component can be moved in a motorized fashion, at least indirectly, using the mount. The line identifiers cooperate with the control and computing unit of the medical device, which controls the motorized displacement of the elements of the mounting, define lines in space having different directions, or having a variable orientation in space. Since the defined lines in space are known to the control and computing unit with reference to their position, in relation to a coordinate system, for example, the ability to move the device component connected to the mount along the defined lines in a linear manner is achieved, in order to obtain a series of X-ray pickups of a body part of a patient. A number of linearly extending lines in space can be combined so as to result in a curved line, along which the device component can be moved. In addition, the device component need not necessarily be moved directly along the defined line, but alternatively can be moved indirectly relative thereto. This means that a line in space can be defined and the device component can be moved along a line which is parallel to this defined line.

In a preferred embodiment of the invention line identifier is formed by a transmitter and a receiver which respectively transmit and receive signal-carrying waves such as ultrasound waves or electromagnetic waves, particularly infrared waves, for example. One or more transmitters can be arranged at the device component, or at a reference point which is determinative for the control of the movement of the device component, and the receivers can be arranged at a defined position within a space in which the medical device is arranged and in which a coordinate system is inscribed. The positions of the receivers in the coordinate system are known to the control and computing unit. If the device component with the transmitter is guided, by means of the control and computing unit, to individual salient points that should be situated on the line in space, i.e. on the line of motion of the device component, then for each of these points in space, the coordinates in a coordinate system can be determined by the control and computing unit (e.g. with the aid of transit time measurements) by means of the emission of signal-carrying waves by the transmitter, which are received by the receiver. The coordinates of the points constitute the supporting points for defining lines by the control and computing unit and are stored by the control and computing unit.

In a variant of the invention the medical device has a reflector which reflects the signal-carrying waves which are emitted by the transmitter. In this variant attachment of the transmitter to the device component can be forgone. The transmitter or transmitters are instead arranged, like the receiver or receivers, in a defined position within the space that accepts the medical device, or within the coordinate system that is inscribed in the space. For defining a point of a line in space, the reflector, which is arranged at the reference point of the device component or is temporarily held at the reference point of the device component, reflects the signal-carrying waves emitted by the transmitter, and the receiver receives the reflected waves. By transit-time measurements, the control and computing unit can subsequently determine the position, i.e. the coordinates of the reflector, or of the reference point of the device component, in the coordinate system, and can store this for defining lines in space. The transmitter preferably transmits waves of varying frequencies, so that, for the determination of the coordinates of the reference point of the device component, or of the point in space, it can distinguish from which transmitter a wave was emitted.

In another variant of the invention the line identifier is a position sensor which detects the location of an element of the mounting and which is electrically connected to the control and computing unit. The device component, for defining a line in space, is controlled by the control and computing unit from a starting position to a point in space that is expected to be situated on the line along which the device component should be at least indirectly moved. When this is done, the position sensor supplies signals to the control and computing unit from which the position of a reference point on the device component can be calculated. With the aid of these signals, the control and computing unit determines and stores the coordinates of the reference point, or of the corresponding point in space in the coordinate system. The starting position, in the coordinate system, of the mount, and thus of the reference point of the device component, thus is known to the control and computing unit.

In an embodiment of the invention, the line identifier has an operating unit which can be actuated manually and/or by means of a foot and/or which receive and process acoustical signals. The operating unit is always actuated when a point in space, to which motorized movement with the mount has proceeded, is to be captured as a supporting point for a line, or its coordinates in the coordinate system are to be determined and stored. As an operating unit that cooperates with the control and computing unit, a voice-activated controller provided with an acoustical receiver such as a microphone can be used, as well as manually activatable devices (such as operating controls, keyboards and joysticks), or foot switches.

In a preferred embodiment of the invention the mount is an articulated arm which is provided with a number of elements that can be moved relative to one another in a motorized fashion, and that the device component is a C-arm that carries an X-ray source and an X-ray receiver. A medical device so constructed is advantageously suitable for a series of X-ray pickups of a body part of a patient along a rectilinear line in space, such as is desirable in the medical field of orthopedics.

DESCRIPTION OF THE PREFERRED EMBODIMENTS

Figure 1:
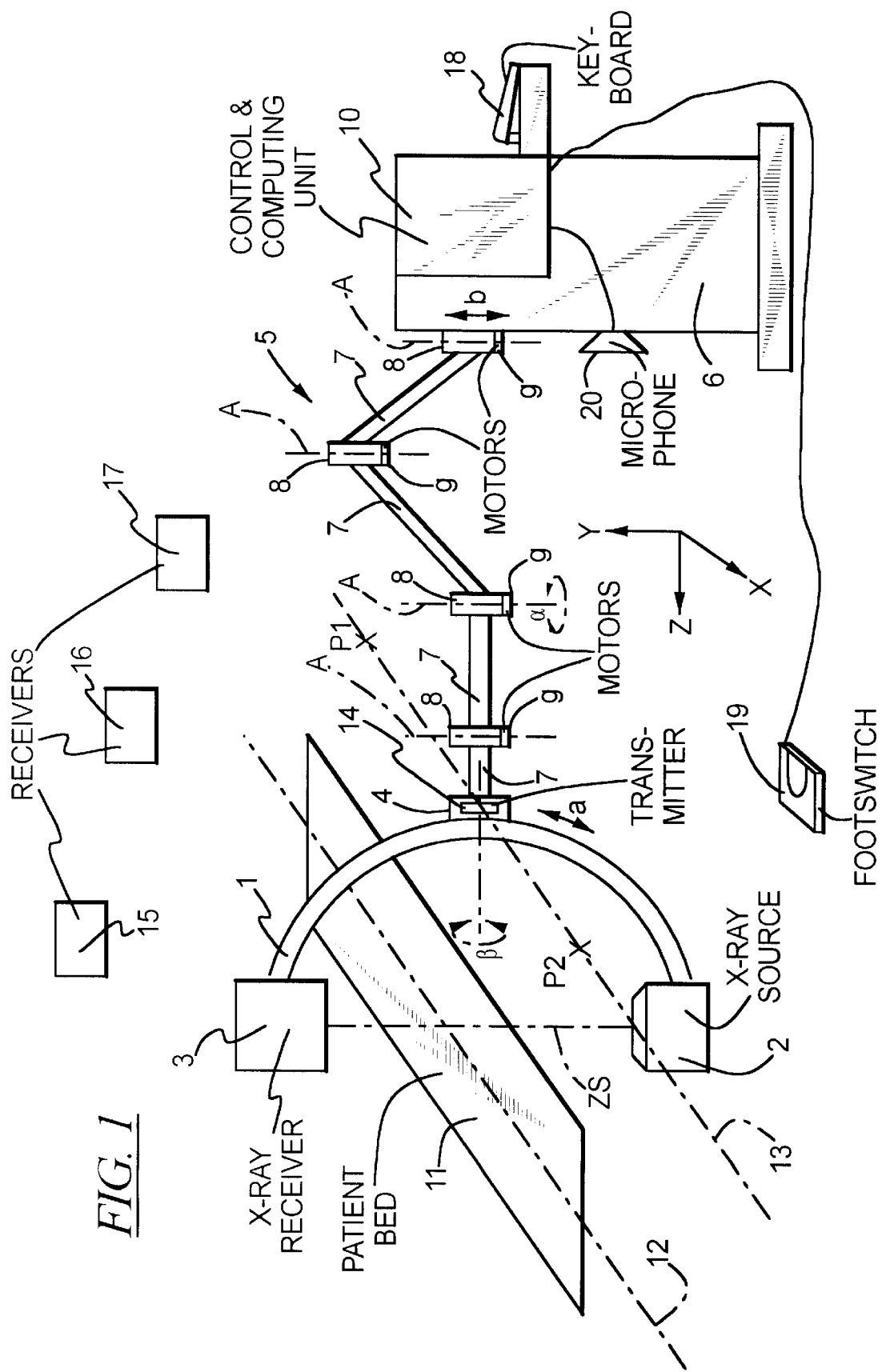
FIG. 1 is a schematic illustration of an inventive medical device with a line identifier formed by transmitters and receivers.

FIG. 1 depicts an inventive medical device in a simplified view. The medical device is an X-ray device in the present exemplary embodiment.

As the aforementioned device component, the X-ray device has a C-arm 1, which is provided with an X-ray source 2 and an X-ray receiver 3 and which is connected, via a holder 4, to a mount which is constructed as an articulated arm 5. The C-arm 1 is mounted in the holder 4 in known fashion so as to be displaceable along its perimeter (cf. double arrow a).

The articulated arm 5 has a number of elements 7 which are connected to one another via joints 8. Each of the joints 8 contains an electromotor 9 which cooperates with the respective joint 8 such that the elements 7, which are fixedly connected to portions (not illustrated) of the joints 8 that can be moved relative to one another, can be moved relative to one another in a motorized fashion. In the exemplary embodiment, the relative movements of the elements 7 result from a motor-controlled rotation of the portions of the joints 8, that are fixedly connected to the elements 7, around an axis A of the joints 8 which extends substantially vertically (cf. double arrow $\alpha$).

The articulated arm 5 is arranged with a joint 8 at a device base 6 and is connected to the holder 4 of the C-arm 1 with an element 7. The holder 4 is mounted against this element 7 such that the holder 4 can be pivoted, together with the C-arm 1, around an axis B (schematically illustrated) extending substantially horizontally (cf. double arrow $\beta$). The joint arranged at the device base 6 can be displaced vertically in a motorized fashion (cf. double arrow b).

The device base 6 stands on the floor of a space which accepts the X-ray device and is provided with a control and computing unit 10 which, in the exemplary embodiment, is a conventional computer (not illustrated) with input means and storage media that are known. The control and computing unit 10 is electrically connected (not illustrated) to the electromotors 9 of the joint 8. The control and computing unit 10 controls the electromotors 9 of the joints 8 such that the elements 7 of the articulated arm 5 correspondingly move relative to one another depending on the specified control instructions, thus moving the C-arm 1 to the position specified to the control and computing unit 10, for example.

A patient bed 11 is also schematically illustrated in FIG. 1, on which patients can be borne for diagnostic radiography, in a manner which is not illustrated. The X-ray device illustrated in FIG. 1 is provided for a series of X-ray pickups along a line in space, as is desirable for orthopedic examinations of body parts of patients, for example. FIG. 1 shows a line 12 as an example, which extends substantially horizontally in a rectilinear manner and along which a series of X-ray pickups are to be taken, this line being arbitrarily selected in the present case. To accomplish this, the C-arm 1 must be moved along a line in space 13 that is parallel to the line 12 such that, given moving of the C-arm 1 along the line 13, the center beam ZS of an X-ray beam proceeding from the X-ray source 2 to the X-ray receiver 3 moves rectilinearly along the line 12. In the exemplary embodiment, the center beam ZS is situated at a right angle to the line 12.

To be able to move the center beam ZS optimally linearly along the line 12, the line 13, along which the C-arm 1 moves at least indirectly rectilinearly, must be defined. In the exemplary embodiment illustrated in FIG. 1, to define the line 13 and thus also the line 12, a line identifier is provided in the form of a transmitter 14 and three receivers 15 to 17. In the exemplary embodiment, the transmitter 14 is arranged at the holder 4 of the C-arm 1. The receivers 15 to 17 are arranged at defined points in the space which accepts the X-ray device. Both the transmitter 14 and the receivers 15 to 17 are electrically connected (not illustrated) to the control and computing unit 10 for transmitting information or control instructions.

The receivers 15 to 17 assume defined positions relative to a coordinate system which is inscribed in the space, or which is allocated to the X-ray device (a Cartesian system in the exemplary embodiment), this position being known to the control and computing unit 10; i.e., the coordinates of the receivers 15 to 17 in the Cartesian coordinate system are known to the control and computing unit 10.

The line 13 is defined in the exemplary embodiment by the corresponding selection of two points through which the line 13 is to extend. The line indicator includes an operating unit which is connected to the control and computing unit 10. In the exemplary embodiment, the operating unit can be formed by a keyboard 18, a footswitch 19, and means a voice-actuated controller that cooperate with the control and computing unit 10. The voice-actuated controller can include a microphone 20, via which acoustical voice instructions can be acoustically captured for voice-controlled operation of the control and computer unit 10, which operation is known per se. The operating unit can be used in parallel or alternatively to one another.

If a physician intends to take a series of X-ray pickups along the line 12, for example, he or she can so move the C-arm 1, by means of the operating unit or units that can be part of the input means of the control and computing unit 10, or by means of separately implemented control means of the control and computing unit 10, so that the center beam ZS of the X-ray beam intersects the desired line of motion, i.e. the line 12, in a starting position. In the exemplary embodiment, this corresponds to the position of the C-arm 1, or of the holder 4 with the transmitter 14, at the point P1. To determine the coordinates of the point P1, which are necessary for defining the line 13 along which the C-arm 1 is to be moved, at least indirectly, the transmitter 14 is prompted via the control and computing unit 10, by means of one of the alternative available operating unit, to emit a signal-carrying electromagnetic wave. The receivers 15 to 17, which are suitable for receiving signal-carrying electromagnetic waves, receive the emitted signal-carrying electromagnetic wave emitted by the transmitter 14. By measuring the respective transit times of the signal-carrying electromagnetic wave between the transmitter 14 and the receivers 15 to 17, the control and computing unit 10, which is connected to the transmitter 14 and the receivers 15 to 17, can determine the coordinates of the point P1 on the basis of the known position of the receivers 15 to 17 in the Cartesian coordinate system. The coordinates of the point P1 are stored in a storage medium of the control and computing unit 10 which is known. The physician subsequently moves the C-arm 1, or the center beam ZS, to a second position, at which the last pickup of the series of X-ray pickups of the patient is to occur. The motion of the C-arm 1 is in turn controlled by the control and computing unit 10, which correspondingly actuates the electromotors 9 of the joints 8 of the joint arm 5 for the execution of the motions. In the exemplary embodiment, this corresponds to the position of the C-arm 1, or of the holder 4 with the transmitter 14, at the point P2. As described above, the coordinates of the point P2 are determined by means of an emission of a signal-carrying electromagnetic wave by the transmitter 14, which the receivers 15 to 17 receive, and by means of transit time measurements. Subsequent to the determination and storage of the coordinates of the point P2, the control and computing unit 10 can unambiguously make the line 13 through the points P1 and P2, along which line the holder 4, or the transmitter 14 arranged at the holder 4, and so indirectly the C-arm 1, are to move for the X-ray pickups. For the rectilinear movement of the C-arm 1 along the line 13, the control and computing unit 10 also calculates intermediate values.

Subsequent to defining the line 13, the C-arm 1 can be moved in a defined manner at least indirectly rectilinearly along the line 13 for taking a series of X-ray pickups (exposures) along the line 12, the electromotors 9 of the joints 8 of the articulated arm 5 being correspondingly actuated by the control and computing unit 10 for the relative movements of the elements 7.

Figure 2:
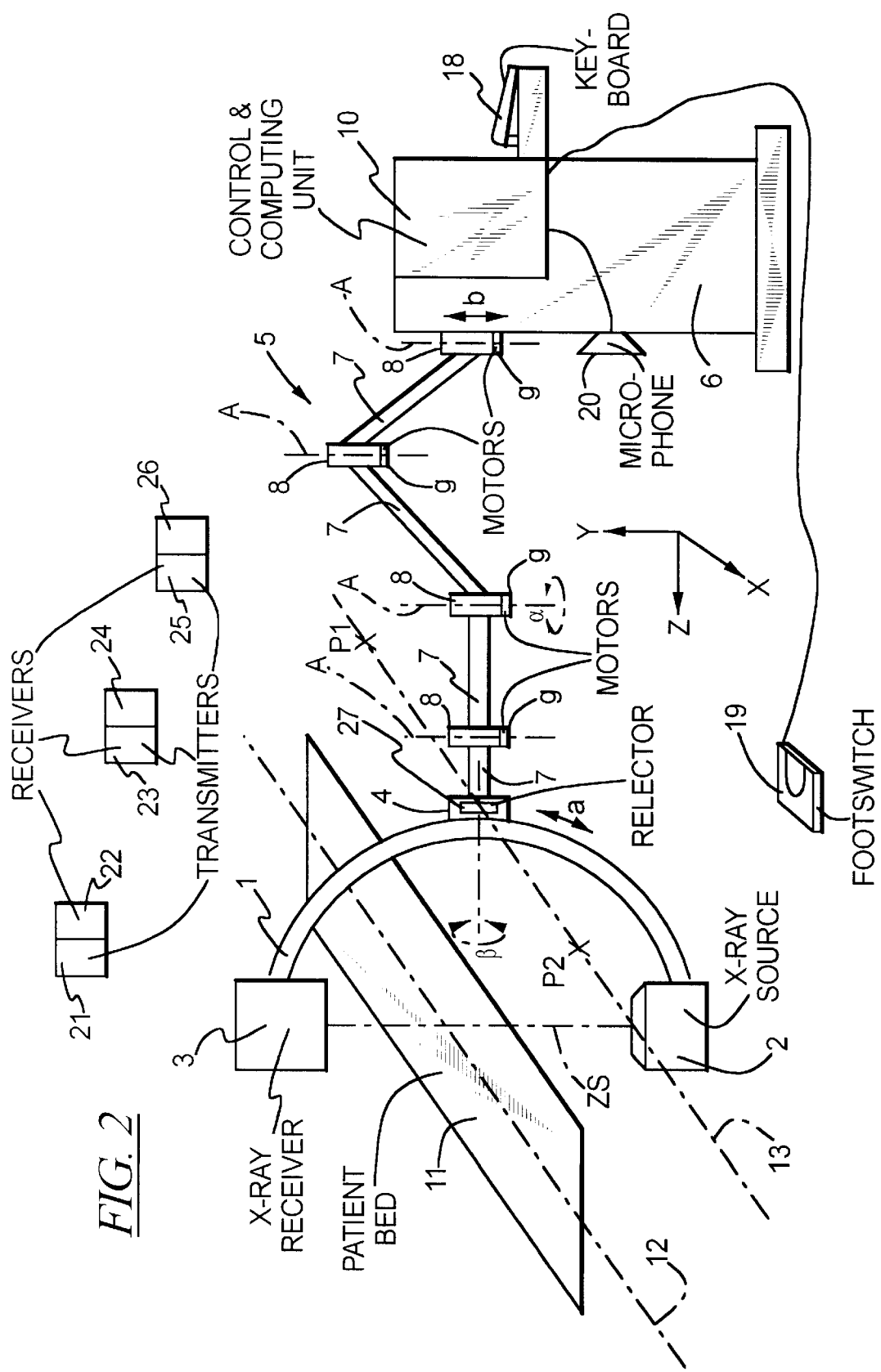
FIG. 2 is a schematic illustration of an inventive device with a line identifier including an arrangement for reflecting waves.

FIG. 2 illustrates a second embodiment of the inventive medical device. The medical device illustrated in FIG. 2 is the same type of X-ray device illustrated in FIG. 1. Components of the X-ray device in FIG. 2 which are essentially identical functionally and structurally to components of the X-ray device of FIG. 1 are provided with the same reference characters.

Unlike in the X-ray device according to FIG. 1, in the X-ray device according to FIG. 2 there are a number of transmitters 21, 23, 25 and receivers 22, 24, 26 with exactly one receiver 22, 24, 26 being allocated to each transmitter 21, 23, 25. The transmitters and receivers 21 to 26 are arranged at defined points in the space that accepts the X-ray device; i.e., the coordinates of the transmitters and receivers 21 to 26 are known to the control and computing unit 10 in reference to the Cartesian coordinate system. Unlike the embodiment illustrated in FIG. 1, a reflector 27 is arranged at the holder 4 instead of a transmitter, which can reflect the waves emitted by the transmitter.

In the procedure for defining the line 13 through the two points P1 and P2, by means of the control and computing unit 10, the C-arm 1 is first moved to the corresponding position from which the series of X-ray pickups along a desired line, namely the line 12, is to occur. In the exemplary embodiment, the C-arm 1, or the holder 4, is located at the position of the point P1. To determine the coordinates of the point P1, the transmitters 21, 23, and 25 are prompted, by one of the control units, to emit signal-carrying electromagnetic waves. The signal-carrying electromagnetic waves are reflected at the reflector 27 and are received by the receivers 22, 24, and 26. To be able to distinguish which wave has been emitted by which transmitters 21, 23, or 25, the transmitters 21, 23, 25 emit waves of respectively different frequencies. In this way, the receivers 22, 24, 26 can unambiguously determine the transmitter from which an electromagnetic wave, reflected at the reflector 27, originated, so that the coordinates of the point P1 in the Cartesian coordinate system can be determined by means of the control and computing unit 10, using transit time measurements, e.g. the transit time of the wave between the transmitter 21 and the receiver 22. The coordinates are stored in a storage medium of the control and computing unit 10 for defining the line 13. The C-arm 1 is subsequently moved, by the control and computing unit 10 to the end position for the series of X-ray pickups, which corresponds to the position of the point P2 for the C-arm 1, or for the reflector 27 of the holder 4. The determination of the coordinates of the point P2 occurs in the above described manner by the emission of signal-carrying electromagnetic waves of the transmitters 21, 23, 25, the reflection of the electromagnetic waves at the reflector 27, the reception of the electromagnetic waves by the receivers 22, 24, 26 and the evaluation of their respective transit times. The line 13 along which the reflector 27 of the holder 4, or indirectly the C-arm 1, can be moved is defined by the two points P1, P2, so that, along the line 12 that is parallel to the line 13, a series of X-ray pickups of a body part of a patient (not illustrated) is possible. The center beam ZS moves rectilinearly along the line 12.

The reflector 27 need not necessarily be connected to the holder 4. The reflector 27 need only be temporarily attached or held to a reference point which is determinative for the displacement of the C-arm 1 for the identification of the coordinates of the reference point, and then can be put aside.

Light waves or infrared waves are possible signal-carrying electromagnetic waves for determining the coordinates of points. A signal-carrying wave means a modulated wave.

However, the transmitters and receivers 21 to 26 of the X-ray device of FIG. 2, as well as the transmitter 14 and the receivers 15 to 17 of the X-ray device of FIG. 1, need not necessarily transmit or receive electromagnetic waves, but can also transmit or receive ultrasound waves.

Moreover, there need not be exactly three receivers in the exemplary embodiment according to FIG. 1, and there need not be exactly three transmitters and receivers in the exemplary embodiment according to FIG. 2. Such a number of receivers is only necessary when the coordinates of a point in space are to be determined. If it is only necessary to determine the coordinates of a point in a plane, a lower number of transmitters or receivers suffices.

In the exemplary embodiment according to FIG. 1, instead of the transmitter 14, a receiver can be arranged at the holder 4. In this case, three corresponding transmitters are arranged at defined positions in the space that accepts the X-ray device.

Figure 3:
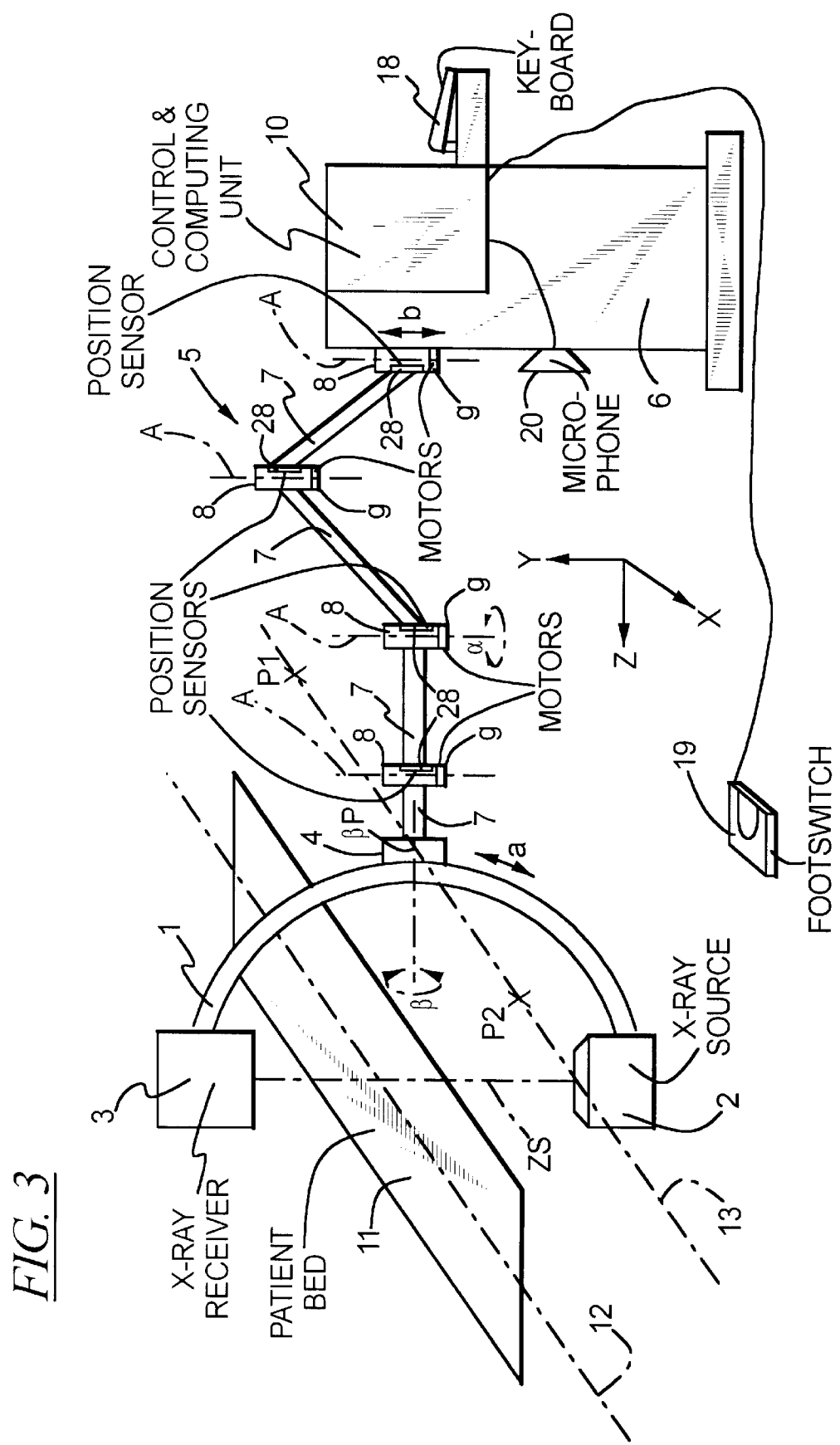
FIG. 3 is a schematic illustration of an inventive device with a line identifier formed by position locators which detect the position of an element of the mount.

FIG. 3 illustrates a third embodiment of the inventive medical device. The medical device illustrated in FIG. 3 is the same type of X-ray device illustrated in FIG. 1.

Unlike the X-ray device from FIG. 1, the X-ray device according to FIG. 3 does not have transmitters and receivers. For the determination of a reference point BP which is arbitrarily selected at the mounting part 4, position sensors 28 are allocated to the electromotors 9 of the joints 8, the position sensors 28 being electrically connected to the control and computing unit 10. Using signals emitted by the position sensors 28, the control and computing unit 10 can always determine the position of the reference point BP in the Cartesian coordinate system.

To define the line 13 along which the reference point BP is to be moved rectilinearly so that the center beam ZS of the X-ray beam moves rectilinearly along the line 12 that is parallel to the line 13, the C-arm 1 is moved by means of the control and computing unit 10 to a first position, which constitutes the starting position for the rectilinear movement of the center beam ZS for the X-ray examination of a patient in the form of a series of X-ray pickups. In the exemplary embodiment, the position of the reference point BP corresponds to the position of the point P1. The control and computing unit 10 can determine the Cartesian coordinates of the reference point BP, or of the point P1 using the signals of the position sensors 28, given the activation of one of the operating unit. The C-arm 1 is subsequently moved into the end position for the rectilinear movement along the line 12 or 13, whereby, in the exemplary embodiment, the reference point BP becomes situated at the point P2. Given the activation of one of the control unit, the control and computing unit 10 can, in turn, determine the coordinates of the reference point BP, or of the point in space P2, with signals from the position sensors 28, and can define the line 13 through the points in space P1 and P2.

Using the signals from the position sensors 28 of the joints 8, a line in space can be defined along which the C-arm 1 can be at least indirectly moved, it being possible to take series of X-ray pickups of a patient along a line parallel to the defined line.

The mounting of the device component need not necessarily be implemented as an articulated arm 5, but can also be implemented as a telescoping arm, for example.

In addition, the device component need not be constructed in the form of a C-arm, but can also be constructed otherwise.

The medical device can be arranged at the ceiling or the wall of a room instead of on the floor.

In the exemplary embodiments described above, only one line 13 was defined in space. However, it is also possible in the framework of the invention to define a number of lines with respectively different directions in space, which need not necessarily proceed horizontally.

The inventive medical device is described above as an X-ray device, but the medical device need not necessarily be an X-ray device.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical device comprising:
   a device component;
   an X-ray source and an X-ray receiver carried by said device component;
   a mount connected to said device component for supporting and positioning said device component, said mount comprising a plurality of motorized elements which are movable relative to each other;
   a control and computing unit for operating said motorized elements to move said motorized elements relative to each other to move said device component; and
   a line identifier arrangement connected to said control and computing unit for providing information to said control and computer unit to determine a plurality of lines in space proceeding along respectively different directions, said control and computing unit using said information to control operation of said motorized elements to move said device component rectilinearly along a line relative to at least one of said different directions.

2. A medical device as claimed in claim 1 wherein said line identifier arrangement comprises a transmitter and receiver which respectively transmit and receive signal-carrying waves for producing said information.

3. A medical device as claimed in claim 1 wherein one of said transmitter and said receiver is co-movable with said device component.

4. A medical device as claimed in claim 2 further comprising a reflector which is co-movable with said device component which reflects said signal-carrying waves from said transmitter to said receiver.

5. A medical device as claimed in claim 1 wherein said line identifier arrangement comprises a plurality of position sensors respectively associated with said motorized elements, electrically connected to said control and computing unit for supplying signals to said control and computing unit identifying the respective positions of said motorized elements.

6. A medical device as claimed in claim 1 further comprising at least one operating unit connected to said control and computing unit for activating said line identifier arrangement.

7. A medical device as claimed in claim 6 wherein said operating unit comprises units selected from the group consisting of a manually actuatable unit, a foot actuatable unit, and a voice-actuated unit.

8. A medical device as claimed in claim 1 wherein said mount comprises an articulated arm comprising said plurality of motorized elements.

9. A medical device as claimed in claim 1 wherein said device component comprises a C-arm.

* * * * *